(12) United States Patent
Koll et al.

(10) Patent No.: US 10,950,329 B2
(45) Date of Patent: Mar. 16, 2021

(54) HYBRID HUMAN AND COMPUTER-ASSISTED CODING WORKFLOW

(71) Applicant: MModal IP LLC, Franklin, TN (US)

(72) Inventors: Detlef Koll, Pittsburgh, PA (US);
Michael Finke, Pittsburgh, PA (US);
John McKenna, Cumming, GA (US);
Derek Nichols, Douglasville, GA (US)

(73) Assignee: MMODAL IP LLC, Franklin, TN (US)

( * ) Notice: Subject to any disclaimer, the term of this patent is extended or adjusted under 35 U.S.C. 154(b) by 468 days.

(21) Appl. No.: 14/941,445

(22) Filed: Nov. 13, 2015

(65) Prior Publication Data

US 2016/0267232 A1 Sep. 15, 2016

Related U.S. Application Data

(60) Provisional application No. 62/132,715, filed on Mar. 13, 2015.

(51) Int. Cl.
*G16H 10/60* (2018.01)
*G06Q 10/10* (2012.01)

(52) U.S. Cl.
CPC ............. *G16H 10/60* (2018.01); *G06Q 10/10* (2013.01)

(58) Field of Classification Search
CPC .............................. G06F 19/328; G16H 10/60
See application file for complete search history.

(56) References Cited

U.S. PATENT DOCUMENTS

| 5,065,315 | A | 11/1991 | Garcia |
| 5,148,366 | A | 9/1992 | Buchanan |
| 5,359,509 | A | 10/1994 | Little |
| 5,483,443 | A | 1/1996 | Milstein et al. |

(Continued)

FOREIGN PATENT DOCUMENTS

| EP | 687987 B1 | 6/2003 |
| EP | 1361522 A2 | 11/2003 |

(Continued)

OTHER PUBLICATIONS

Daugherty B. et al., "Tracking Incidental Findings", Radiology Today, Jul. 2014, vol. 15, No. 7, p. 6.

(Continued)

*Primary Examiner* — Reginald R Reyes
(74) *Attorney, Agent, or Firm* — Blueshift IP, LLC; Robert Plotkin

(57) ABSTRACT

A computer system increases the efficiency with which billing codes may be generated based on a chart, such as a medical chart. The computer system provides the chart to a computer-assisted coding (CAC) module, which produces an initial set of billing codes and an initial assessment of the accuracy and/or completeness of the codes. The computer system decides whether to send the initial set of billing codes to an initial human reviewer. If the computer system sends the initial set of billing codes to the initial human reviewer, then the initial human reviewer reviews the chart and the output of the CAC module, and attempts to fix errors in the CAC output. The system provides the chart and the current (initial or modified) codes to a final human reviewer, who may be more highly skilled than the initial human reviewer, for final verification and modification.

12 Claims, 2 Drawing Sheets

(56) References Cited

U.S. PATENT DOCUMENTS

| | | |
|---|---|---|
| 5,664,109 A | 9/1997 | Johnson et al. |
| 5,823,948 A | 10/1998 | Ross et al. |
| 5,933,809 A | 8/1999 | Hunt |
| 6,006,183 A | 12/1999 | Lai et al. |
| 6,345,249 B1 | 2/2002 | Ortega |
| 6,377,922 B2 | 4/2002 | Brown |
| 6,529,876 B1 | 3/2003 | Dart et al. |
| 6,655,583 B2 | 12/2003 | Walsh |
| 6,662,168 B1 | 12/2003 | Wallach et al. |
| 6,738,784 B1 | 5/2004 | Howes |
| 6,834,264 B2 | 12/2004 | Lucas |
| 6,915,254 B1 | 7/2005 | Heinze |
| 7,233,938 B2 | 6/2007 | Carus |
| 7,236,968 B2 | 6/2007 | Seki et al. |
| 7,313,515 B2 | 12/2007 | Crouch et al. |
| 7,379,946 B2 | 5/2008 | Carus |
| 7,447,988 B2 | 11/2008 | Ross |
| 7,467,094 B2 | 12/2008 | Rosenfeld |
| 7,519,529 B1 | 4/2009 | Horvitz |
| 7,584,103 B2 | 9/2009 | Fritsch |
| 7,613,610 B1 | 11/2009 | Zimmerman |
| 7,650,628 B2 | 1/2010 | Zimmerman |
| 7,716,040 B2 | 5/2010 | Koll |
| 7,725,330 B2 | 5/2010 | Rao |
| 7,818,186 B2 | 10/2010 | Bonissone |
| 7,869,998 B1 | 1/2011 | Fabbrizio et al. |
| 7,885,811 B2 | 2/2011 | Zimmerman |
| 8,024,196 B1 | 9/2011 | Wodtke |
| 8,050,938 B1 | 11/2011 | Green, Jr. |
| 8,311,854 B1 | 11/2012 | Stanley |
| 8,359,297 B2 | 1/2013 | Garrett |
| 8,392,216 B2 | 3/2013 | Crockett |
| 8,452,609 B2 | 5/2013 | Berg |
| 8,463,673 B2 | 6/2013 | Koll |
| 8,468,167 B2 | 6/2013 | Sathyanarayana |
| 8,583,439 B1 | 11/2013 | Kondziela |
| 8,781,829 B2 | 7/2014 | Koll |
| 8,781,853 B2 | 7/2014 | Green, III |
| 8,862,483 B2 | 10/2014 | Scarola |
| 9,082,310 B2 | 7/2015 | Koll |
| 9,275,643 B2 | 3/2016 | Koll |
| 9,424,523 B2 | 8/2016 | Koll |
| 9,679,077 B2 | 6/2017 | Jaganathan et al. |
| 9,704,099 B2 | 7/2017 | Koll |
| 9,996,510 B2 | 6/2018 | Koll |
| 10,156,956 B2 | 12/2018 | Koll |
| 10,325,296 B2 | 6/2019 | Koll |
| 2001/0042080 A1 | 11/2001 | Ross |
| 2002/0029161 A1* | 3/2002 | Brodersen .......... G06Q 10/1093 |
| | | 705/7.14 |
| 2002/0065854 A1 | 5/2002 | Pressly |
| 2002/0077819 A1 | 6/2002 | Girardo |
| 2002/0099717 A1 | 7/2002 | Bennett |
| 2002/0120466 A1 | 8/2002 | Finn |
| 2002/0198741 A1 | 12/2002 | Randazzo |
| 2003/0018470 A1 | 1/2003 | Golden |
| 2003/0074248 A1 | 4/2003 | Braud |
| 2003/0133156 A1* | 7/2003 | Cragun .............. H04N 1/00326 |
| | | 358/1.18 |
| 2003/0154085 A1 | 8/2003 | Kelley |
| 2003/0229614 A1 | 12/2003 | Kotler |
| 2004/0044546 A1 | 3/2004 | Moore |
| 2004/0078215 A1 | 4/2004 | Dahlin et al. |
| 2004/0128163 A1 | 7/2004 | Goodman |
| 2004/0240720 A1 | 12/2004 | Brantley |
| 2004/0243545 A1 | 12/2004 | Boone et al. |
| 2004/0254816 A1 | 12/2004 | Myers |
| 2005/0071194 A1 | 3/2005 | Bormann et al. |
| 2005/0102140 A1 | 5/2005 | Davne et al. |
| 2005/0137910 A1 | 6/2005 | Rao |
| 2005/0158767 A1 | 7/2005 | Haskell |
| 2005/0171819 A1* | 8/2005 | Keaton ................ G06Q 40/08 |
| | | 705/4 |
| 2005/0203775 A1 | 9/2005 | Chesbrough |
| 2005/0228815 A1 | 10/2005 | Carus et al. |
| 2005/0240439 A1 | 10/2005 | Covit |
| 2005/0251422 A1 | 11/2005 | Wolfman |
| 2006/0020492 A1 | 1/2006 | Cousineau |
| 2006/0020493 A1 | 1/2006 | Cousineau |
| 2006/0020886 A1 | 1/2006 | Agrawal |
| 2006/0036472 A1 | 2/2006 | Crockett |
| 2006/0041428 A1 | 2/2006 | Fritsch |
| 2006/0041836 A1 | 2/2006 | Gordon |
| 2006/0047539 A1 | 3/2006 | Huang |
| 2006/0074656 A1 | 4/2006 | Mathias |
| 2006/0122865 A1 | 6/2006 | Preiss |
| 2006/0129435 A1 | 6/2006 | Smitherman et al. |
| 2006/0178908 A1 | 8/2006 | Rappaport |
| 2006/0190263 A1 | 8/2006 | Finke |
| 2006/0277073 A1 | 12/2006 | Heilbrunn |
| 2006/0282302 A1 | 12/2006 | Hussain |
| 2007/0013968 A1 | 1/2007 | Ebaugh |
| 2007/0016450 A1 | 1/2007 | Bhora |
| 2007/0016451 A1 | 1/2007 | Tilson |
| 2007/0033073 A1 | 2/2007 | Tajaliawal |
| 2007/0050187 A1 | 3/2007 | Cox |
| 2007/0067185 A1 | 3/2007 | Halsted |
| 2007/0088564 A1 | 4/2007 | March |
| 2007/0106751 A1 | 5/2007 | Moore |
| 2007/0112599 A1 | 5/2007 | Liu |
| 2007/0118410 A1 | 5/2007 | Nadai |
| 2007/0143141 A1 | 6/2007 | Villasenor et al. |
| 2007/0198907 A1 | 8/2007 | Degala |
| 2007/0203708 A1 | 8/2007 | Polcyn |
| 2007/0226211 A1 | 9/2007 | Heinze et al. |
| 2007/0276649 A1 | 11/2007 | Schubert |
| 2007/0299665 A1 | 12/2007 | Koll |
| 2008/0004505 A1 | 1/2008 | Kapit |
| 2008/0077451 A1 | 3/2008 | Anthony |
| 2008/0168343 A1 | 7/2008 | Doganata |
| 2008/0228769 A1 | 9/2008 | Lita |
| 2008/0249374 A1 | 10/2008 | Morita |
| 2009/0048833 A1 | 2/2009 | Fritsch |
| 2009/0187407 A1 | 7/2009 | Soble |
| 2009/0192800 A1 | 7/2009 | Brandt |
| 2009/0192822 A1 | 7/2009 | Regulapati |
| 2009/0228126 A1 | 9/2009 | Spielberg |
| 2009/0228299 A1 | 9/2009 | Kangarloo et al. |
| 2009/0271218 A1 | 10/2009 | Mok |
| 2009/0287678 A1 | 11/2009 | Brown |
| 2010/0036680 A1 | 2/2010 | Familant |
| 2010/0063907 A1 | 3/2010 | Savani |
| 2010/0094657 A1 | 4/2010 | Stern |
| 2010/0100570 A1 | 4/2010 | Constantin et al. |
| 2010/0114598 A1 | 5/2010 | Oez |
| 2010/0125450 A1 | 5/2010 | Michaelangelo |
| 2010/0138241 A1 | 6/2010 | Ruark |
| 2010/0217624 A1 | 8/2010 | Kay |
| 2010/0250236 A1 | 9/2010 | Jagannathan |
| 2010/0299135 A1 | 11/2010 | Fritsch |
| 2010/0299320 A1 | 11/2010 | Claud et al. |
| 2010/0305997 A1 | 12/2010 | Ananian |
| 2011/0166875 A1 | 7/2011 | Hayter |
| 2011/0202370 A1 | 8/2011 | Green |
| 2011/0239146 A1 | 9/2011 | Dutta et al. |
| 2011/0295864 A1 | 12/2011 | Betz et al. |
| 2011/0301978 A1 | 12/2011 | Shiu |
| 2012/0010900 A1 | 1/2012 | Kaniadakis |
| 2012/0016690 A1 | 1/2012 | Ramarajan et al. |
| 2012/0041950 A1 | 2/2012 | Koll |
| 2012/0065987 A1 | 3/2012 | Farooq et al. |
| 2012/0166220 A1 | 6/2012 | Baldwin |
| 2012/0185275 A1 | 7/2012 | Loghmani |
| 2012/0215551 A1 | 8/2012 | Flanagan |
| 2012/0215782 A1 | 8/2012 | Jagannathan |
| 2012/0239429 A1 | 9/2012 | Corfield |
| 2012/0323572 A1 | 12/2012 | Koll |
| 2012/0323598 A1* | 12/2012 | Koll ...................... G06Q 30/04 |
| | | 705/2 |
| 2013/0006667 A1 | 1/2013 | Green |
| 2013/0110547 A1 | 5/2013 | Englund et al. |
| 2013/0144651 A1 | 6/2013 | Rao |
| 2013/0159408 A1 | 6/2013 | Winn |
| 2013/0226617 A1 | 8/2013 | Mok |

(56) References Cited

U.S. PATENT DOCUMENTS

| | | |
|---|---|---|
| 2013/0238330 A1 | 9/2013 | Casella Dos Santos |
| 2014/0006431 A1 | 1/2014 | Jagannathan |
| 2014/0047375 A1 | 2/2014 | Koll |
| 2014/0108047 A1 | 4/2014 | Kinney |
| 2014/0164197 A1 | 6/2014 | Koll |
| 2014/0278553 A1 | 9/2014 | Fritsch |
| 2014/0324423 A1 | 10/2014 | Koll |
| 2014/0343963 A1 | 11/2014 | Fritsch |
| 2015/0066537 A1 | 3/2015 | Sheffer et al. |
| 2015/0088504 A1 | 3/2015 | Jagannathan |
| 2015/0134349 A1* | 5/2015 | Vdovjak .......... G06Q 10/06395 705/2 |
| 2015/0278449 A1 | 10/2015 | Laborde |
| 2015/0310362 A1 | 10/2015 | Huffman |
| 2015/0356198 A1 | 12/2015 | D'Souza et al. |
| 2015/0356647 A1 | 12/2015 | Reiser et al. |
| 2015/0371145 A1 | 12/2015 | Koll |
| 2016/0012345 A1 | 1/2016 | Hewitt |
| 2016/0093010 A1 | 3/2016 | Vasiliu-Feltes et al. |
| 2016/0147955 A1 | 5/2016 | Shah |
| 2016/0166220 A1 | 6/2016 | Bar-Shalev |
| 2016/0179770 A1 | 6/2016 | Koll |
| 2016/0294964 A1 | 10/2016 | Brune |
| 2016/0335554 A1 | 11/2016 | Koll |
| 2016/0371447 A1 | 12/2016 | Koman |
| 2017/0068781 A1 | 3/2017 | Zasowski |
| 2017/0270626 A1 | 9/2017 | Koll |
| 2018/0040087 A1 | 2/2018 | Koll |
| 2018/0081859 A1 | 3/2018 | Snider |
| 2018/0101879 A1 | 4/2018 | Koll |
| 2018/0276188 A1 | 9/2018 | Koll |
| 2019/0026436 A1 | 1/2019 | Bender |
| 2019/0065008 A1 | 2/2019 | Koll |

FOREIGN PATENT DOCUMENTS

| | | |
|---|---|---|
| EP | 2030196 B1 | 9/2018 |
| EP | 2883203 B1 | 10/2018 |
| EP | 3571608 A1 | 11/2019 |
| JP | H09106428 A | 4/1997 |
| JP | 2002207823 | 7/2002 |
| JP | 2004157815 | 6/2004 |
| JP | 2005025418 | 1/2005 |
| JP | 2005267358 | 9/2005 |
| JP | 2006072436 | 3/2006 |
| JP | 2006509295 A | 3/2006 |
| JP | 4037250 B2 | 1/2008 |
| JP | 2008108021 A | 5/2008 |
| JP | 2008250378 | 10/2008 |
| JP | 2009211157 | 9/2009 |
| JP | 2011118538 | 6/2011 |
| JP | 6215383 | 9/2016 |
| JP | 6339566 B | 5/2018 |
| JP | 6388864 B2 | 9/2018 |
| WO | 2005122002 | 12/2005 |
| WO | 2009143395 A1 | 11/2009 |
| WO | 2011100474 A2 | 8/2011 |
| WO | 2011100474 A3 | 1/2012 |
| WO | 2012048306 | 4/2012 |
| WO | 2012177611 | 12/2012 |
| WO | 2014120501 | 8/2014 |
| WO | 2015079354 | 6/2015 |
| WO | 2015079354 A1 | 6/2015 |
| WO | 2018136417 | 7/2018 |
| WO | 2019103930 | 5/2019 |

OTHER PUBLICATIONS

Yildiz M.Y. et al., "A text processing pipeline to extract recommendations from radiology reports", Journal of Biomedical Informatics, 2013, vol. 46, pp. 354-362.

OpenVPMS, Follow-up tasks, Submitted by Matt C on Fri, Sep. 17, 2010, Available at: https://openvpms.org/project/followup-task-lists-enhancements.

Adam E.J.et al., "ESR guidelines for the communication of urgent and unexpected findings" European Society of Radiology (ESR), 2011, vol. 3, Issue (1), pp. 1-3.

"xPatterns Clinical Auto-Coding," Atigeo, Whitepaper, pp. 8 (2014).

Anonymous: "Medical transcription—Wikipedia", Feb. 13, 2010, XP055465109, Retrieved from the Internet: URL: https://en.wikipedia.org/w/index.php?title=Medical_transcription&oldid=343657066 [Retrieved on Apr. 6, 2018].

Examiner's Report dated Apr. 15, 2019 in Canadian patent application No. 2,875,584, 4 pages.

Non-Final Rejection dated Jun. 19, 2019 in U.S. Appl. No. 15/872,532 of Gilan El Saadawi, filed Jan. 16, 2018, 54 pages.

Petition for Inter Parties Review of U.S. Pat. No. 8,781,829 filed before the Patent Trial and Appeal Board on Dec. 21, 2018 by PetitionerNuance Communications, Inc., 81 pages.

Exhibit 1003 of Petition for Inter Parties Review of U.S. Pat. No. 8,781,829 filed before the Patent Trial and Appeal Board on Dec. 21, 2018 by Petitioner Nuance Communications, Inc., Declaration of Andrew Sears.

Exhibit 1004 of Petition for Inter Parties Review of U.S. Pat. No. 8,781,829 filed before the Patent Trial and Appeal Board on Dec. 21, 2018 by Petitioner Nuance Communications, Inc., Curriculum Vitae of Andrew Sears.

Exhibit 1005 of Petition for Inter Parties Review of U.S. Pat. No. 8,781,829 filed before the Patent Trial and Appeal Board on Dec. 21, 2018 by Petitioner MModal Services Ltd., Michael Freeman Bliss, "Speech Recognition for Health Professionals", Pearson Prentice Hall, pp. 18-24, (2005).

Exhibit 1007 of Petition for Inter Parties Review of U.S. Pat. No. 8,781,829 filed before the Patent Trial and Appeal Board on Dec. 21, 2018 by Petitioner Nuance Communications, Inc., Panzarasa et al., "Technical Solutions for Integrating Clinical Practice Guidelines with Electronic Patient Records", pp. 141-154, (2010).

Exhibit 1009 of Petition for Inter Parties Review of U.S. Pat. No. 8,781,829 filed before the Patent Trial and Appeal Board on Dec. 21, 2018 by Petitioner Nuance Communications, Inc., Joel D. Miller and Elizabeth M. Wenzel, "Recent Developments in SLAB: A Software-Based System for Interactive Spatial Sound Synthesis", Proceedings of 2002, Int'l Conf. on Auditory Display, pp. IDAC02 1-6, Jul. 2-5, 2002.

Exhibit 1010 of Petition for Inter Parties Review of U.S. Pat. No. 8,781,829 filed before the Patent Trial and Appeal Board on Dec. 21, 2018 by Petitioner MModal Services Ltd., JCAHO—Specification Manual for National Implementation of Hospital Core Measures, Version 2.0 (Mar. 1, 2004).

Exhibit 1011 of Petition for Inter Parties Review of U.S. Pat. No. 8,781,829 filed before the Patent Trial and Appeal Board on Dec. 21, 2018 by Petitioner MModal Services Ltd., JCAHO—Introduction and Background.

Exhibit 1012 of Petition for Inter Parties Review of U.S. Pat. No. 8,781,829 filed before the Patent Trial and Appeal Board on Dec. 21, 2018 by Petitioner Nuance Communications, Inc., JCAHO—Using the Specifications Manual for National Implementation of Hospital Core Measures.

Exhibit 1013 of Petition for Inter Parties Review of U.S. Pat. No. 8,412,524 filed before the Patent Trial and Appeal Board on Dec. 21, 2018 by Petitioner Nuance Communications, Inc., W. H. Auden, "Menu Selection and Form Filling", Semantic Organization, Chapter 3, 1970.

Exhibit 1014 of Petition for Inter Parties Review of U.S. Pat. No. 8,781,829 filed before the Patent Trial and Appeal Board on Dec. 21, 2018 by Petitioner MModal Services Ltd., Alan J. Dix et al., "Human-Computer Interaction", 2nd ed., pp. 130-137, (1998).

Exhibit 1015 of Petition for Inter Parties Review of U.S. Pat. No. 8,781,829 filed before the Patent Trial and Appeal Board on Dec. 21, 2018 by Petitioner Nuance Communications, Inc., Frequently Asked Questions: Signature Requirements, Cahaba Government Benefit Administrators (Mar. 2011).

Exhibit 1016 of Petition for Inter Parties Review of U.S. Pat. No. 8,781,829 filed before the Patent Trial and Appeal Board on Dec. 21, 2018 by Petitioner Nuance Communications, Inc., WayBackMachine

(56) References Cited

OTHER PUBLICATIONS capture of CDC Website ICD-9-CM classification explanation, available at https://web.archive.org/web/20110430031819/https://www.cdc.gov/nchs/icd/icd9cm.htm (Apr. 30, 2011).
Exhibit 1017 of Petition for Inter Parties Review of U.S. Pat. No. 8,781,829 filed before the Patent Trial and Appeal Board on Dec. 21, 2018 by Petitioner MModal Services Ltd., MModal's Preliminary Claim Construction Disclosure, *MModal Services Ltd v. Nuance Communications, Inc.*, Case No. 1:18-cv-00901-WMR (N.D. Ga. Dec. 3, 2018).
Exhibit 1018 of Petition for Inter Parties Review of U.S. Pat. No. 8,781,829 filed before the Patent Trial and Appeal Board on Dec. 21, 2018 by Petitioner Nuance Communications, Inc., JCAHO Facts, Joint Commission on Accreditation of Healthcare Organizations, (Aug. 1, 2005).
Exhibit 1019 of Petition for Inter Parties Review of U.S. Pat. No. 8,781,829 filed before the Patent Trial and Appeal Board on Dec. 21, 2018 by Petitioner Nuance Communications, Inc., Roe, D. B., & Wilpon, J. G. (Eds.). Voice communication between humans and machines. National Academies Press., pp. 165-198 (1994).
Exhibit 1020 of Petition for Inter Parties Review of U.S. Pat. No. 8,781,829 filed before the Patent Trial and Appeal Board on Dec. 21, 2018 by Petitioner MModal Services Ltd., Win Phillips, "Introduction to Natural Language Processing, Consortium on Cognitive Science Instruction (Apr. 1999)", available at https://web.archive.org/web/20090221020728/http:/www.mind.ilstu.edu/curriculum/protothinker/natural_language_processing.php (Sep. 1, 2006).
Exhibit 1021 of Petition for Inter Parties Review of U.S. Pat. No. 8,781,829 filed before the Patent Trial and Appeal Board on Dec. 21, 2018 by Petitioner Nuance Communications, Inc., Laurence S. Gillick, "A Rapid Match Algorithm for Continuous Speech Recognition", HLT 1990 Proceedings of the Workshop on Speech and Natural Language, pp. 170-172, (Jun. 24, 1990).
Exhibit 1022 of Petition for Inter Parties Review of U.S. Pat. No. 8,781,829 filed before the Patent Trial and Appeal Board on Dec. 21, 2018 by Petitioner Nuance Communications, Inc., Declaration of Dr. James Mullins regarding public availability of Panzarasa, pp. 1-66.
Exhibit 1022 of Petition for Inter Parties Review of U.S. Pat. No. 8,781,829 filed before the Patent Trial and Appeal Board on Dec. 21, 2018 by Petitioner MModal Services Ltd., Declaration of Dr. James Mullins regarding public availability of Panzarasa, pp. 67-110.
Exhibit 1022 of Petition for Inter Parties Review of U.S. Pat. No. 8,781,829 filed before the Patent Trial and Appeal Board on Dec. 21, 2018 by Petitioner Nuance Communications, Inc., Declaration of Dr. James Mullins regarding public availability of Panzarasa, pp. 111-153.
Exhibit 1022 of Petition for Inter Parties Review of U.S. Pat. No. 8,781,829 filed before the Patent Trial and Appeal Board on Dec. 21, 2018 by Petitioner Nuance Communications, Inc., Declaration of Dr. James Mullins regarding public availability of Panzarasa, pp. 154-201.
Exhibit 1022 of Petition for Inter Parties Review of U.S. Pat. No. 8,781,829 filed before the Patent Trial and Appeal Board on Dec. 21, 2018 by Petitioner Nuance Communications, Inc., Declaration of Dr. James Mullins regarding public availability of Panzarasa, pp. 202-243.
Exhibit 1022 of Petition for Inter Parties Review of U.S. Pat. No. 8,781,829 filed before the Patent Trial and Appeal Board on Dec. 21, 2018 by Petitioner MModal Services Ltd., Declaration of Dr. James Mullins regarding public availability of Panzarasa, pp. 244-273 end.
Examiner's Report dated Dec. 20, 2018 in Canadian patent application No. 2,839,266, 4 pages.
International Search Report and Written Opinion received for PCT Patent Application No. PCT/US2018/061517, dated Mar. 7, 2019, 10 pages.
"Medical Decision Making and the Marshfield Clinic Scoring Tool FAQ," American College of Emergency Physicians, May 24, 2017, 3 pages [online: https://www.acep.org/administration/reimbursement/reimbursement-faqs/medical-decision-making-and-the-marshfield-clinic-scoring-tool-faq/#sm.000019luk7uslud34somv72pq17x3].
Anonymous: "DMXzone Universal Form Validator PHP", Sep. 2, 2009, XP055432714, [online: https://www.dmxzone.com/Downloads/Tutorial_FormValidatorPHP_update.zip/FormValidatorPHP_update.pdf].
Centers for Medicare & Medicaid Services, "Medicare Physician Guide: 1995 Documentation Guidelines for Evaluation and Management Services," 1995, 16 pages [online: https://www.cms.gov/Outreach-and-Education/Medicare-Learning-Network-MLN/MLNEdWebGuide/Downloads/95Docguidelines.pdf].
Centers for Medicare & Medicaid Services, "Medicare Physician Guide: 1997 Documentation Guidelines for Evaluation and Management Services ," 1997, 49 pages [online: https://www.cms.gov/Outreach-and-Education/Medicare-Learning-Network-MLN/MLNEdWebGuide/Downloads/97Docguidelines.pdf].
Examination Report received in Canadian patent application No. 2,791,292 dated Sep. 19, 2018, 9 pages.
Final Office Action dated Sep. 4, 2018 in U.S. Appl. No. 14/218,220 of Juergen Fritsch, filed Mar. 18, 2014, 46 pages.
James Flanagan, et al. "Defining the Standards for Automated E&M Coding Through Coding Consistency Methodology," Perspectives in Health Information Management, CAC Proceedings; Fall 2008, 7 pages [online: http://perspectives.ahima.org/defining-the-standards-for-automated-eam-coding-through-coding-consistency-methodology/].
Non-Final Office Action dated Sep. 4, 2018 in U.S. Appl. No. 15/839,037 of Detlef Koll, filed Dec. 12, 2017, 22 pages.
Stephanie L. Jones "E/M Audit Tool: To be used with AAPC Specialty examinations," 2006 reprinted by American Academy of Professional Coders, 2 pages [online: https://c.ymcdn.com/sites/www.txosteo.org/resource/resmgr/imported/EM%20AuditTool%20from%20Practicum.pdf].
Summons to Attend Oral Proceedings pursuant to Rule 115(1) EPC mailed Oct. 31, 2018, in European Patent Application No. 12802338.9, 8 pages.
Slabodkin Greg, "CMS proposed rulereduces Evaluation andManagement coding burden",Jul. 13, 2018, 4 pages, "https://www.healthdatamanagement.com/news/cms-proposed-rule-reduces-evaluation-and-management-coding-burden?reconf=1".
Communication pursuant to Article 94(3) EPC dated Jan. 8, 2019 by the European Patent Office in patent application No. 13809956.9, 5 pages.
Arup 106428 et al., "Context-based Speech Recognition Error Detection and Correction," Proceedings of HLT-NAACL 2004: Short Papers, May 2004, 4 pages.
Communication Pursuant to Article 94(3) EPC, dated Jun. 27, 2019, in EPO application No. 14762803.6, 11 pages.
Dimick, Chris, "Quality Check: An Overview of Quality Measures and Their Uses," Journal of AHIMA 81, No. 9 (Sep. 2010); 34-38, Retrieved on May 14, 2013 from http://library.ahima.org/xpedio/groups/public/documents/ahima/bok1_047952.hcsp?DocName=bok1_047952.
Examination Report received in Canadian patent application No. 2,791,292 dated Aug. 2, 2019, 7 pages.
Examiner's Report dated Jun. 27, 2019 in Canadian Patent Application No. 2,881,564, 6 pages.
First Examination Report in Indian patent application No. 2186/MUMNP/2012 dated Jul. 19, 2019, 7 pages.
First Examination Report dated Aug. 29, 2019 in Indian patent application No. 448/MUMNP/2013, 6 pages.
International Preliminary Report on Patentability, dated Aug. 1, 2019 in International Patent Application No. PCT/US2018/013868, 9 pages.
International Search Report and Written Opinion received for PCT Patent Application No. PCT/US2018/013868, dated Jun. 18, 2018, 14 pages.
Summons to Attend Oral Proceedings Pursuant to Rule 115(1) EPC mailed Jun. 12, 2019 in European Patent Application No. 11748231.5, 11 pages.
Examination Report dated Jun. 18, 2019, in Canadian patent application No. 2,811,942, 6 pages.

(56) References Cited

OTHER PUBLICATIONS

Decision to Refuse European Application dated Oct. 24, 2019 in European Patent Application No. 11748231.5, 19 pages.
Examiner's Report dated Nov. 29, 2019 in Canadian patent application No. 2,839,266, 4 pages.
Final Rejection dated Nov. 27, 2019 for U.S. Appl. No. 15/872,532 of Gilan El Saadawi, filed Jan. 16, 2018, 33 pages.
First Examination Report dated Dec. 24, 2019, in Indian patent application No. 336/DELNP/2014, 7 pages.
First Examination Report dated Oct. 7, 2019 in Indian patent application No. 7449/DELNP/2012, 9 pages.
Non-Final Rejection dated Jan. 9, 2020 for U.S. Appl. No. 15/788,522 of Detlef Koll, filed Oct. 19, 2017, 55 pages.
Second Examiners Report dated May 20, 2020, in Canadian patent application No. 2,875,584, 5 pages.
Notice of Allowance dated Sep. 11, 2020 for U.S. Appl. No. 16/174,503 of Detlef Koll, filed Oct. 30, 2018, 33 pages.
Non Final Rejection dated Apr. 3, 2020 for U.S. Appl. No. 15/872,532 of Gilan El Saadawi, filed Jan. 16, 2018, 22 pages.
Non Final Rejection dated Apr. 6, 2020 for U.S. Appl. No. 15/616,884 of Detlef Koll, filed Jun. 7, 2017, 7 pages.
Non Final Rejection dated May 14, 2020 for U.S. Appl. No. 16/193,443 of Derek L. Nichols, filed Nov. 16, 2018, 64 pages.
Final Rejection dated Mar. 16, 2020 for U.S. Appl. No. 15/993,958 of Detlef Koll, filed May 31, 2018, 33 pages.
Non Final Rejection dated Mar. 19, 2020 for U.S. Appl. No. 16/174,503 of Detlef Koll, filed Oct. 30, 2018, 43 pages.
Final Rejection dated Jul. 14, 2020 for U.S. Appl. No. 15/788,522 of Detlef Koll, filed Oct. 19, 2017, 33 pages.
Final Rejection dated Jul. 21, 2020 in U.S. Appl. No. 15/872,532 of Gilan El Saadawi, filed Jan. 16, 2018, 38 pages.
Non Final Rejection dated Jun. 10, 2020 for U.S. Appl. No. 15/993,958 of Detlef Koll, filed May 31, 2018, 14 pages.
Examination Report received in Canadian patent application No. 2,791,292 dated Mar. 9, 2020, 3 pages.
Examination Report dated Feb. 4, 2020, in Canadian patent application No. 2,904,656, 5 pages.
Summons to Attend Oral Proceedings Pursuant to Rule 115(1) EPC mailed Mar. 24, 2020, by the European Patent Office in patent application No. 13809956.9, 10 pages.

\* cited by examiner

HYBRID HUMAN AND COMPUTER-ASSISTED CODING WORKFLOW

BACKGROUND

After physicians and other healthcare professionals (referred to herein generally as "healthcare providers") provide healthcare services to patients, bills for such services must be generated. The process of generating such bills based on the set of clinical reports associated with a patient encounter (referred to as a "chart") can be a tedious, time-consuming, risky, and error-prone process for a variety of reasons, such as:

Laws, regulations, and institutional policies prescribe that bills satisfy various rules, such as rules requiring that each item in a bill be justified by adequate supporting evidence. Such rules can be difficult to identify and interpret, and the required evidence can be difficult to find and evaluate.

Bills must be encoded using billing codes specified by technical billing code standards such as ICD-9, ICD-10, and CPT. Such standards can be difficult to understand and apply in particular situations in light of the services provided and the available evidence. Furthermore, as older standards (such as ICD-9) are replaced with newer, more complex, standards (such as ICD-10), the difficulty of understanding the applicable standards is increasing.

Bills often must be generated quickly due to time and budget constraints.

The error rate in bills, including both false positives and false negatives, must be kept to a minimum. False positives (including items in bills that should not be included, such as because they are not justified by available evidence) may violate applicable laws, regulations, and/or institutional policies. False negatives (failing to include items in bills that should be included) lead to lost revenue for the healthcare provider.

Billing codes are typically generated by specialized "billing coders," who must be trained to select the appropriate codes based on the documentation provided by the healthcare providers. Training a billing coder can be time-consuming and expensive, and even expert billing coders can make mistakes.

These problems are likely to be exacerbated by the transition to the ICD-10 billing code standard. Expert billing coders, who are fluent in ICD-10, are in short supply and are unlikely to meet the demand for such billing coders.

In order to address this shortfall in supply of expert billing coders, many healthcare providers have either been outsourcing their coding process to service companies or attempting to automate the coding process using Computer Assisted Coding (CAC) technology.

Both outsourcing and automation have associated drawbacks. For example, because the ability to perform billing coding accurately and completely directly impacts the cash flow and overall profitability of healthcare organizations, such organizations are reluctant to rely on an outsourced workforce. Another drawback of outsourced billing coding is that the ultimate responsibility, and legal liability, for the accuracy of billing coding lies with the healthcare organization, few (if any) outsourced billing coding providers are willing to indemnify a sizable healthcare organization against liability incurred as the result of billing coding errors. As a result, even healthcare organizations that are willing to outsource may not be able to outsource all of their billing coding needs to billing coding providers who can satisfy exacting quality and legal requirements.

CAC solutions have their own problems. CAC solutions apply Natural Language Processing (NLP) technology to compute the most likely set of billing codes from a set of clinical reports before a human coder reviews the chart. Some CAC solutions can, in addition, create confidence scores that estimate the likelihood that any given code, or the complete coding of a chart, is correct. Some CAC solutions provide the option of bypassing the human coder completely, for at least a subset of charts, if the chart-level confidence score is sufficiently high. The state of the art of such fully-automated coding, however, is not sufficiently accurate to be relied upon in practice for anything but the most simple charts. More complex charts, which are the norm in practice, cannot be accurately coded using fully-automated coding. As a result, in practice it is necessary, in most cases, for a human coder to review the automatically-generated codes for accuracy and to revise such codes as necessary.

The promise of CAC solutions, even when the codes that they generate must be reviewed by a human coder, is to provide an increase in efficiency in comparison with a system that relies solely on human coders, by providing the initial set of codes for review quickly and accurately enough that the combination of generating codes automatically followed by human review and correction of those codes is more efficient and inexpensive than purely human code generation. In practice, however, CAC systems do not always increase productivity as much as is theoretically possible. Furthermore, deploying CAC systems requires a lengthy and labor-intensive tuning process to adapt the CAC technology to the idiosyncrasies of a healthcare provider. The result is that productivity during the tuning process can be impacted negatively, and the resulting overall productivity may be lower than if no CAC system were used at all.

What is needed, therefore, are techniques for overcoming the problems of conventional CAC systems, and for otherwise improving the efficiency of generating billing codes.

SUMMARY

A computer system increases the efficiency with which billing codes may be generated based on a chart, such as a medical chart. The computer system provides the chart to a computer-assisted coding (CAC) module, which produces an initial set of billing codes and an initial assessment of the accuracy and/or completeness of the codes. The computer system decides whether to send the initial set of billing codes to an initial human reviewer. If the computer system sends the initial set of billing codes to the initial human reviewer, then the initial human reviewer reviews the chart and the output of the CAC module, and attempts to fix errors in the CAC output. The system provides the chart and the current (initial or modified) codes to a final human reviewer, who may be more highly skilled than the initial human reviewer, for final verification and modification.

Other features and advantages of various aspects and embodiments of the present invention will become apparent from the following description and from the claims.

DETAILED DESCRIPTION

Figure 1:
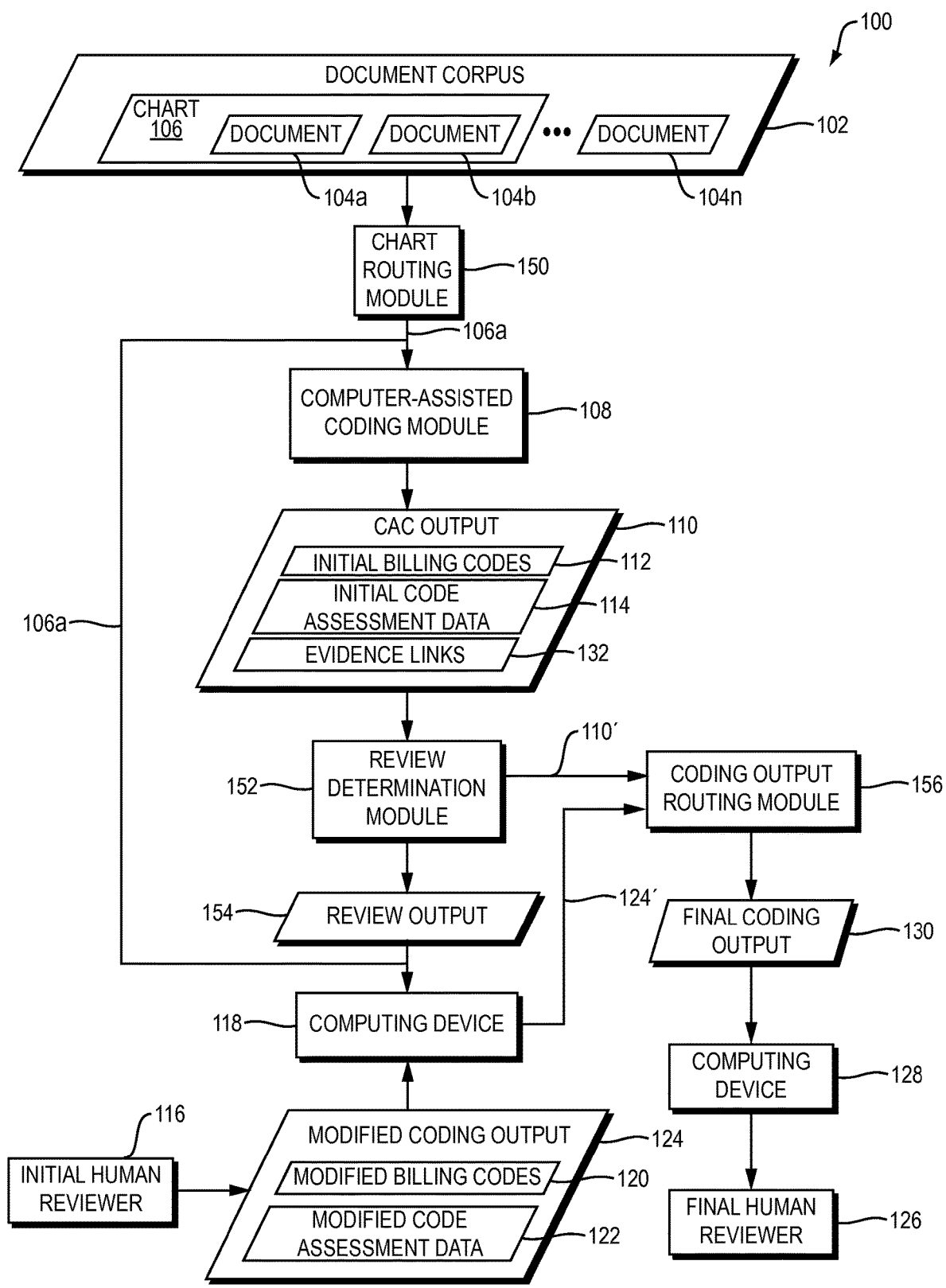
FIG. 1 is a dataflow diagram of a system for generating billing codes according to one embodiment of the present invention.
Figure 2:
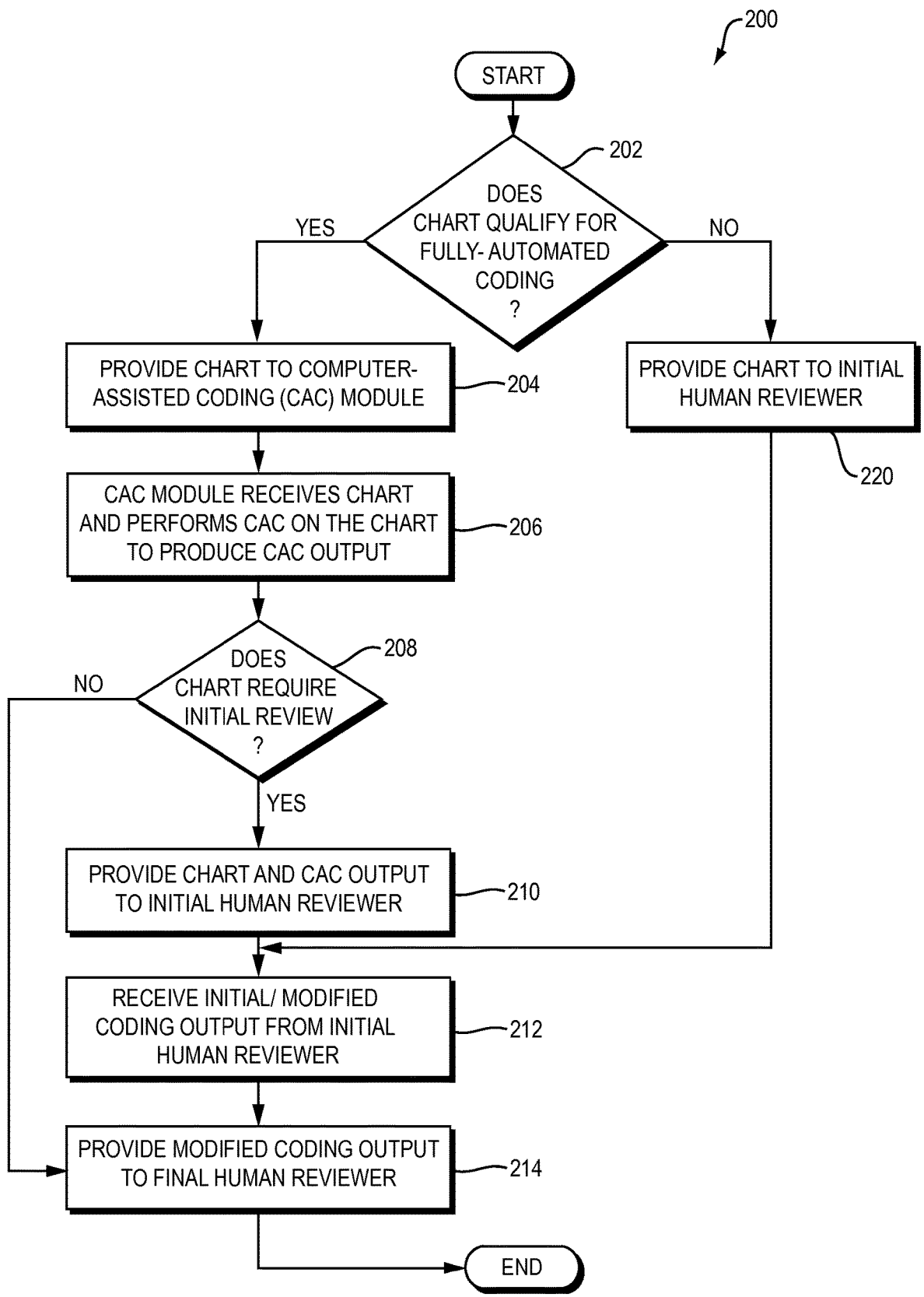
FIG. 2 is a flowchart of a method performed by the system of FIG. 1 according to one embodiment of the present invention.

Embodiments of the present invention include computer systems which may be used to improve the efficiency with which billing codes may be generated. Referring to FIG. 1, a dataflow diagram is shown of a system 100 for generating billing codes according to one embodiment of the present invention. Referring to FIG. 2, a flowchart is shown of a method 200 performed by the system 100 of FIG. 1 according to one embodiment of the present invention.

The system 100 includes a document corpus 102, which includes a plurality of documents 104a-n, where n may be any number. The document corpus 102 is merely one example of a "data set" as that term is used herein. The term "document" is used generally herein to include any type of data record, such as a freeform text document (e.g., a plain text document or a document created using a word processing application), a structured document (such as an XML document), a scanned document (e.g., a scan of handwritten progress notes), or a data record in a database. A document may, for example, be an Electronic Medical Record (EMR) or Electronic Health Record (EHR). Structured documents in the document corpus 102 may, for example, have been created using techniques disclosed in U.S. Pat. No. 7,584,103 B2, issued on Sep. 1, 2009, entitled, "Automated Extraction of Semantic Content and Generation of a Structured Document from Speech."

The document corpus 102 may include documents of different types, such as text documents and EHRs. Although FIG. 1 shows just one document corpus 102, the document corpus 102 may include multiple data sets, such as multiple databases, files stored in multiple file systems, multiple EMR/EHR databases, or any combination thereof. As these examples illustrate, the document corpus 102 may include documents stored on a plurality of storage media (e.g., hard drives) and/or maintained by multiple computer systems.

For ease of explanation, certain embodiments will be disclosed herein in connection with documents which take the form of clinical reports describing patient encounters. Examples of clinical reports include admission orders, discharge orders, and prescriptions. A plurality of clinical reports relating to a particular patient encounter is referred to herein as a "chart." Often, the process of generating a set of billing codes involves generating a set of billing codes based on the clinical reports in a particular chart. The resulting billing codes may be represented in any manner, such as according to billing code standards such as any one or more of HL7 CDA v2 XML standard (ANSI-approved since May 2005), SNOMED CT, LOINC, CPT, ICD-9 and ICD-10, and UMLS.

Assume, solely for purposes of example, that the system 100 includes a chart 106, which includes documents 104a-b from the document corpus. As mentioned above, a chart may, more generally, including one or more documents relating to a particular patient encounter. Although the chart 106 is shown as being contained within the document corpus 102 in FIG. 1, the chart 106 need not exist as a data structure within the document corpus 102. Instead, for example, another component of the system 100 may store data (e.g., in a separate database) indicating that the chart 106 includes the documents 104a and 104b.

Now assume that the chart 106 is ready to be used to generate a set of billing codes based on the chart 106. Further assume that the system 100 includes a computer-assisted coding (CAC) module 108. The CAC module 108 may include any number and type of computer hardware, computer software, networking equipment, and interconnections sufficient to enable the CAC module 108 to perform computer-assisted coding. The CAC module 108 is configured to perform, or to attempt to perform, computer-assisted coding without the involvement of a human, except that a human may provide the chart 106 to the CAC module 108 and interpret the output of the CAC module 108.

The system 100 may include a chart routing module 150, which may receive some or all of the chart 106 as input, and which may determine whether the chart 106 qualifies for fully-automated processing by the CAC module 108 (FIG. 2, operation 202). The chart routing module 150 may make this determination in any of a variety of ways. For example, the chart routing module 150 may determine whether the chart 106 includes any scanned handwritten notes and determine that the chart 106 does not qualify for fully-automated processing by the CAC module 108 in response to determining that the chart 106 includes at least one scanned handwritten note. As another example, the chart routing module 150 may determine whether the chart 106 has a high confidence of being coded accurately by the CAC module 108. The chart routing module 150 may make this determination by, for example, determining whether the chart 106 describes a complex medical procedure, and concluding that the chart 106 has a high confidence of being coded accurately by the CAC module 108 only if the chart 106 does not describe a complex medical procedure. The system 100 may determine whether a medical procedure is "complex" in any of a variety of ways, such as by determining whether the procedure lasted more than a predetermined amount of time (e.g., 6 hours), or by determining whether the patient who is the subject of the procedure stayed in the hospital for longer than some predetermined amount of time (e.g., 3 days). As yet another example, the chart routing module 150 may conclude that a medical procedure is "complex" and requires non-automated coding if the lab values of the patient who was the subject of the medical procedure has non-normal lab values. Regardless of how the chart routing module 150 determines that the chart 106 has a high confidence of being coded accurately by the CAC module 108, the chart routing module 150 may determine that the chart 106 qualifies for fully-automated processing by the CAC module 108 in response to determining that the chart 106 has a high confidence of being coded accurately by the CAC module 108.

If the chart routing module 150 determines that the chart 106 qualifies for fully-automated processing, the chart routing module 150 may provide output 106a representing the chart 106 to the CAC module 108 for processing (FIG. 2, operation 204). For ease of explanation, the following description will refer to the CAC module 108 as operating on the chart 106 instead of the chart output 106a. The CAC module 108 may receive the chart 106 and perform computer-assisted coding on the chart 106 to produce CAC output 110 (FIG. 2, operation 206). The CAC output 110 may include one or more of the following:

- A set 112 of initial billing codes, including one or more billing codes generated by the CAC module 108 based on the chart 106.
- Initial code assessment data 114, representing an overall assessment of the completeness and/or correctness of the initial billing codes 112.
- Links 132 to evidence that is relevant to the set 112 of initial billing codes. Such evidence may include, for example, one or both of the following: (1) evidence that was found by the CAC module 108 but that the CAC module did not rely upon to generate the set 112 of initial billing codes; and (2) evidence that was found by the CAC module 108 and that the CAC module did rely upon to generate the set 112 of initial billing codes.

The initial code assessment data 114 may include any of a variety of data. For example the initial code assessment data 114 may include any one or more of the following:

- data representing an overall assessment of the completeness of the initial billing codes 112;
- data representing a completeness confidence score indicating a confidence that the initial billing codes 112 are complete, i.e., that the initial billing codes 112 include all billing codes that can be generated based on the chart 106;
- data representing a correctness confidence score indicating an overall confidence that the initial billing codes 112 are correct, i.e., that the initial billing codes 112 accurately encode billing information for the healthcare services represented by the chart 106; and
- data representing an overall classification of the initial billing codes 112, such as "likely completely correct," "requires review," or "known deficiencies."

The initial code assessment data 114 may indicate that the initial billing codes 112 are likely completely correct based on, for example, a function of the completeness confidence score and/or the correctness confidence score. For example, if the correctness confidence score exceeds a first predetermined threshold (e.g., 95%) and the completeness confidence score exceeds a second predetermined threshold (e.g., 90%), then the system 100 may conclude that the initial billing codes 112 are likely completely correct.

The initial code assessment data 114 may indicate that the initial billing codes 112 contain a known deficiency if, for example, the chart 106 is missing a required report, such as a "Discharge Summary" report.

The system 100 may also include a review determination module 152, which may receive some or all of the CAC output 110 as input, and which may determine whether the initial code assessment data 114 indicates that the chart 106 has been classified as requiring review (FIG. 2, operation 208). If the review determination module 152 determines that the chart 106 has been classified as requiring review, then the review determination module 152 may provide output 154 containing or otherwise representing the chart 106 and the CAC output 110 (or a portion thereof) to an initial human reviewer 116, such as by transmitting the review output 154 (e.g., the chart 106 and CAC output 110) over a network to a computing device 118 used by or otherwise associated with the initial human reviewer 116 (FIG. 2, operation 210). The initial human reviewer 116 may, for example, be a junior or relatively inexperienced and/or unskilled reviewer (e.g., billing coder). If the review determination module 152 determines that the chart 106 has not been classified as requiring review, then the review determination module 152 may produce output 110' representing the CAC output 110, and provide the output to a coding output routing module 156, which is described in more detail below.

Although not shown in FIG. 2 or 3, the review determination module 152 may determine whether providing the CAC output 110 to the initial human reviewer 116 is likely to add value to the CAC output 110, and only provide the CAC output 110 to the initial human reviewer 116 in response to determining that the initial human reviewer 116 is likely to add value to the CAC output 110. For example, the review determination module 152 may determine, in operation 208, whether the chart 106 requires initial human review, and also determine whether review of the CAC output 110 by the initial human reviewer 116 is likely to add value to the CAC output 110, and then only provide the CAC output 110 to the initial human reviewer 116 if the review determination module 152 determined that the chart 106 requires initial human review and that the initial human reviewer 116 is likely to add value to the CAC output 110.

The review determination module 152 may determine whether the initial human reviewer 116 is likely to add value to the CAC output 110 in any of a variety of ways. For example, the review determination module 152 may make this determination in any of the ways disclosed herein by which the chart routing module 150 may determine whether the chart 106 describes a complex medical procedure. The review determination module 152 may, for example, use any such technique to determine whether the CAC output 110 and/or the chart 106 describes a complex medical procedure, and not provide the CAC output 110 to the initial human reviewer 116 in response to determining that the CAC output 110 and/or the chart 106 describes a complex medical procedure.

As another example, the review determination module 152 may determine whether the initial human reviewer 116 is likely to add value to the CAC output 110 by determining whether the initial human reviewer 116 is sufficiently skilled to add value to the CAC output 110. The review determination module 152 may, for example, determine whether the initial human reviewer 116 is sufficiently skilled to add value to the CAC output 110, and not provide the CAC output 110 to the initial human reviewer 116 in response to determining that the initial human reviewer 116 is not sufficiently skilled to add value to the CAC output 110. The review determination module 152 may determine whether the initial human reviewer 116 is sufficiently skilled to add value to the CAC output 110 in any of a variety of ways. For example, the review determination module 152 may determine whether a skill value associated with the initial human reviewer 116 satisfies a skill criterion (e.g., exceeds a maximum predetermined value), and not provide the CAC output 110 to the initial human reviewer 116 in response to determining that the skill value does not satisfy the skill criterion.

If the chart routing module 150 previously determined (in operation 202 of FIG. 2) that the chart 106 did not qualify for fully-automated coding, then the chart routing module 150 may provide the chart 106 to the initial human reviewer 116 (FIG. 2, operation 220). In other words, if the CAC module 108 processes the chart 106 to produce the CAC output 110, then the CAC output 110 may be provided to the initial human reviewer 116, whereas if the CAC module 108 does not process the chart 106, then the chart 106 may be provided to the initial human reviewer 116. If the chart 106 is provided to the initial human reviewer 116, then the initial human reviewer 116 may manually code the chart 106 to produce modified coding output 124, without the use of the CAC module 108. The following discussion, however, assumes that the automatically-generated CAC output 110 is provided to the initial human reviewer 116.

Any of the operations described herein as being performed in connection with the output 110' of the CAC module 108 may alternatively be performed on the output 124' of the initial human reviewer 116 (e.g., if the chart output 106a is provided to the initial human reviewer 116 but not to the CAC module 108). Furthermore, any operations described herein as being performed on the output 110' of the CAC module 108 may be performed on both the output 110' of the CAC module 108 and the output 124' of the initial human reviewer 116.

The initial human reviewer 116 may review the initial billing codes 112 for completeness and/or correctness. Before doing so, however, the initial human reviewer 116 may determine whether to review the initial billing codes 112. For example, the initial human reviewer 116 may determine whether the chart 106 can be coded (i.e., whether the initial billing codes 112 can be modified) with high confidence. If the initial human reviewer 116 determines that the chart 106 cannot be coded with high confidence, then the initial human reviewer 116 may skip the following steps involving reviewing the initial billing codes 112 for completeness and/or correctness.

As another example, the initial human reviewer 116 may determine whether the total amount of reimbursement represented by the chart 106 and/or the initial billing codes 112 exceeds some predetermined threshold amount, such as an average reimbursement amount or an approved reimbursement amount. If the initial human reviewer 116 determines that the total amount of reimbursement exceeds the predetermined threshold amount, then the initial human reviewer 116 may skip the following steps involving reviewing the initial billing codes 112 for completeness and/or correctness.

The initial human reviewer 116 may, based on any combination of the chart 106, the initial billing codes 112, and the initial code assessment 114, modify the initial billing codes 112 in an attempt to increase their completeness and improve their correctness, thereby producing a set of modified billing codes 120. The initial human reviewer 116 may also modify the initial code assessment 114 to indicate, for example, the initial human reviewer 116's assessment of the completeness and/or correctness of the modified billing codes 120, thereby producing a modified code assessment 122. Both the modified billing codes 120 and the modified code assessment 122 may be part of modified coding output 124 produced by the initial human reviewer 116.

The initial human reviewer 116 may also perform additional tasks based on the chart 106 and/or the CAC output 110. One purpose of these additional tasks may be to assist a subsequent human reviewer in reviewing the chart 106 and/or the modified coding output 124. For example, the initial human reviewer 116 may perform any one or more of the following additional tasks based on the chart 106 and/or the CAC output 110:
 sort clinical documents in the chart 106 in order of decreasing relevance;
 mark individual documents within the chart 106 as relevant and/or irrelevant; and
 mark the text positions of relevant portions of documents within the chart 106, and/or extract such relevant portions from the documents.

Data representing the results of any such additional actions may be stored within the modified coding output 124. For example, the modified coding output 124 may include data representing the initial human reviewer 116's selected sort order of documents within the chart 106. The initial human reviewer 116, via the computing device 118, may provide output 124' containing or otherwise representing the modified coding output 124 back to the system 100 (FIG. 2, operation 212).

The system 100 may include a coding output routing module 156. The coding output routing module 156 may provide a final human reviewer 126 with final coding output 130, which may include and/or be derived from either:

the CAC output 110 or 110', if the CAC output 110 was not provided to or modified by the initial human reviewer 116; or
 the modified coding output 124 or 124', if the CAC output 110 was modified by the initial human reviewer 116 to produce the modified coding output 124.

The final coding output 130 may also include the chart 106 and/or data derived from the chart 106. The coding output routing module 156 may, for example, provide the chart 106 and the final coding output 130 to the final human reviewer 126 by transmitting the chart 106 and the final coding output 130 over a network to a computing device 128 used by or otherwise associated with the final human reviewer 126 (FIG. 2, operation 214). The final human reviewer 126 may, for example, be a senior or relatively experienced or expert reviewer (e.g., billing coder), and may be a different person than the initial human reviewer 116. The final coding output 130 may, for example, be:
 the CAC output 110, if the CAC output 110 was not sent to or modified by the initial human reviewer 116, in which case the final coding output 130 may include both the initial billing codes 112 and the initial code assessment 114; or
 the modified coding output 124, if the initial human reviewer 116 modified the CAC output 110 to produce the modified coding output 124, in which case the final coding output may include the modified billing codes 120 and the modified code assessment 122.

The final human reviewer 126 may review the chart 106 and the final coding output 130, and analyze them for any of a variety of purposes. For example, the final human reviewer 126 may choose to perform any one or more of the following, in any combination:
 allow codes classified as "likely completely correct" to be submitted for billing without further review;
 allow codes classified as "likely completely correct" to be submitted for billing without further review, except for a randomly selected sample of codes, which may be processed by a quality assurance procedure to verify their accuracy;
 if the chart 106 (or specific codes therein) has been classified as "requiring further review," then use the modified coding output 124 to code the chart 106 (or the specific codes therein); and
 if the chart 106 (or specific codes therein) has been classified as "known deficiencies," then route the chart (or specified codes therein) to a specialized workflow.

Although FIG. 1 only shows a single chart 106, the system 100 of FIG. 1 may repeat the method 200 of FIG. 2 for any number of charts.

Embodiments of the present invention have a variety of advantages, such as the following. In general, embodiments of the present invention address shortcomings of CAC technology, by allowing healthcare providers to obtain the efficiency benefits of CAC technology, while staying in full control of the coding process and without sacrificing quality. In particular, embodiments of the present invention may use a combination of automated (CAC) technology and human reviewers, structured and sequenced in a particular manner, to leverage the efficiency gains of CAC while using human reviewers to ensure accuracy.

Even more specifically, the use of the initial human reviewer 116 enables the system 100 and method 200 to catch certain errors in the CAC output 110. Using a combination of the CAC module 108 and the initial human reviewer 116 may provide a higher quality output than that produced by the CAC module 108 alone, and at a lower cost than using a highly-trained human reviewer alone, depending on the relative costs and accuracies of the CAC module 108 and the initial human reviewer 116.

Furthermore, the initial human reviewer 116 may be relatively unskilled and be capable of correcting only relatively simple errors. Even so, the system 100 as a whole may be more efficient (measured, for example, in terms of accuracy per unit cost) and/or more accurate overall than the CAC module 108 itself, when the function performed by the final human reviewer 126 is taken into account. For example, if the final human reviewer 126 is an expert billing coder, then the final human reviewer 126 may catch and correct errors produced by the CAC module 108 that were not corrected by the initial human reviewer 116, thereby increasing the accuracy of the final coding output 130. Even if the cost of the final human reviewer 126 is relatively high (as measured, e.g., in terms of hourly wages), the overall cost of the system 100 may still be acceptable if the number of codes reviewed, and therefore the amount of time spent, by the final human reviewer 126 is relatively small. The system 100's use of the CAC module 108 and the initial human reviewer 116, and in particular the system 100's use of the initial code assessment 114 and the modified code assessment 122, enables the system 100 to limit the number of codes that the final human reviewer 126 must review, so that the cost of the final human reviewer 126 is kept low and so that the final human reviewer 126 is used to review and correct only relatively complex codes for which the expert skills of the final human reviewer 126 are required.

In addition to increasing the efficiency of the coding process, the system 100 and method 200 may increase the overall accuracy of the system 100 in comparison to a purely automated system (e.g., the CAC module 108). As described above, the CAC module 108 may produce erroneous codes, especially in complex situations. The initial human reviewer 116 and the final human reviewer 126 may correct such codes. As a result, the system 100 may increase the accuracy of the final coding output 130 in comparison to the automatically-generated codes 112 produced by the CAC module 108.

One benefit of the system 100, therefore, is that it uses the CAC module 108 to produce the codes 112 automatically, and that it performs additional steps which increase the accuracy of the final coding output 130 in comparison to the codes 112 produced solely by the CAC module 108. The system 100 may, therefore, be seen as an improved computer system for generating billing codes. The system 100, therefore, solves the technical problem of how to increase the accuracy of the codes produced by a computer-automated coding module.

Furthermore, the system 100 and method 200 enable certain charts to be coded (at least in part) automatically, while also enabling codes to be generated based on charts containing clinical reports that cannot be processed automatically, such as clinical reports in the form of scanned handwritten notes. The system 100 and method 200 may code such clinical reports by routing those reports to the initial human reviewer 116, who may generate an initial set of codes, and by then routing the initial set of codes to the final human reviewer 126 for review and correction. In this way, the system 100 and method 200 obtain the advantages of both the automated CAC module 108 and of the manual skill of the initial human reviewer 116 and the final human reviewer 126.

As described above, one function performed by the chart routing module 150 is to determine whether the chart 106 is to determine whether the chart 106 qualifies for fully-automated processing by the CAC module 108. Another, related, function performed by the chart routing module 150 is to determine the right time at which to submit the chart 106 to the CAC module 108 and/or to a human coder for coding. For example, the chart routing module 150 may be adapted not to submit the chart 106 (e.g., to the CAC module 108) for coding unless and until a discharge summary has been received (e.g., unless and until the chart 106 includes a discharge summary). The chart routing module 150 may further be adapted to submit the chart 106 (e.g., to the CAC module 108) after some predetermined maximum amount of time has passed, even if no discharge summary has been received (e.g., even if the chart 106 does not include a discharge summary). This is merely one example of a way in which the chart routing module 150 may determine the right time at which to submit the chart 106 for coding.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

Any of the functions disclosed herein may be implemented using means for performing those functions. Such means include, but are not limited to, any of the components disclosed herein, such as the computer-related components described below.

The techniques described above may be implemented, for example, in hardware, one or more computer programs tangibly stored on one or more computer-readable media, firmware, or any combination thereof. The techniques described above may be implemented in one or more computer programs executing on (or executable by) a programmable computer including any combination of any number of the following: a processor, a storage medium readable and/or writable by the processor (including, for example, volatile and non-volatile memory and/or storage elements), an input device, and an output device. Program code may be applied to input entered using the input device to perform the functions described and to generate output using the output device.

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

Any data disclosed herein may be implemented, for example, in one or more data structures tangibly stored on a non-transitory computer-readable medium. Embodiments of the invention may store such data in such data structure(s) and read such data from such data structure(s).

What is claimed is:

1. A method performed by at least one computer processor executing computer program instructions stored on at least one non-transitory computer-readable medium, the method comprising:
   (A) receiving, by a chart routing module executed by the at least one computer processor, data representing a medical chart;
   (B) determining, by the chart routing module, whether the medical chart qualifies for automated processing by a computer-assisted coding (CAC) module, wherein determining whether the medical chart qualifies for the automated processing comprises:
      determining whether the medical chart has a high confidence of being coded accurately by the CAC module, comprising determining whether the medical chart describes a complex medical procedure;
   (C) in response to determining that the medical chart does not describe a complex medical procedure:
      providing, by the chart routing module, the medical chart to the CAC module;
      performing CAC, by the CAC module, on the medical chart to produce an initial set of billing codes automatically;
      receiving, by the chart routing module, the initial set of billing codes from the CAC module;
      determining, by the chart routing module, whether a skill value associated with an initial reviewer exceeds a particular value;
      providing, by the chart routing module, the initial set of billing codes to the initial reviewer in response that the skill value associated with the initial reviewer exceeds the particular value;
      receiving, by the chart routing module, from the initial reviewer, a modified set of billing codes and modified code assessment data that represents an assessment of accuracy and completeness of the modified set of billing codes; and
      providing, by a coding output routing module executed by the at least one computer processor, a final coding output for a final review, wherein the final coding output comprises the medical chart, the modified code assessment data, and the modified set of billing codes, and wherein providing the final coding output for the final review results in correctness of errors in the modified set of billing codes received from the initial reviewer and increase in efficiency of a coding process, which lead to increase in accuracy of the final coding output and reduction in costs associated with the coding process; and
   (D) in response to determining that the medical chart describes a complex medical procedure:
      providing the medical chart to the initial reviewer;
      receiving the initial set of billing codes from the initial reviewer; and
      providing the initial set of billing codes for the final review, wherein providing the initial set of billing codes for the final review results in correctness of errors in the initial set of billing codes.

2. The method of claim 1, wherein the data representing the medical chart includes data representing a freeform text document.

3. The method of claim 1, wherein the data representing the medical chart includes data representing a structured document.

4. The method of claim 3, wherein the data representing the structured document comprises data representing an XML document.

5. The method of claim 1, wherein the data representing the medical chart comprises data representing a data record in a database.

6. The method of claim 1, wherein the data representing the medical chart includes data representing at least two of: a freeform text document, an XML document, and a data record in a database.

7. A system comprising at least one non-transitory computer-readable medium storing computer program instructions executable by at least one computer processor to perform a method, the method comprising:
   (A) receiving, by a chart routing module executed by the at least one computer processor, data representing a medical chart, wherein the chart routing module is configured to perform one or more routing determinations on the data;
   (B) determining, by the chart routing module, whether the medical chart qualifies for automated processing by a computer-assisted coding (CAC) module, wherein determining whether the medical chart qualifies for the automated processing comprises one of:
      determining whether the medical chart comprises scanned handwritten notes; and
      determining whether the medical chart has a high confidence of being coded accurately by the CAC module;
   (C) in response to determining that the medical chart qualifies for the automated processing by the CAC module:
      providing, by the chart routing module, the medical chart to the CAC module;
      performing CAC, by the CAC module, on the medical chart to produce an initial set of billing codes automatically;
      receiving, by the chart routing module, the initial set of billing codes from the CAC module;
      determining, by the chart routing module, whether a skill value associated with an initial reviewer exceeds a particular value;
      providing, by the chart routing module, the initial set of billing codes to the initial reviewer in response to determining that the skill value associated with the initial reviewer exceeds the particular value;

receiving, by the chart routing module, from the initial reviewer, a modified set of billing codes and modified code assessment data that represents an assessment of accuracy and completeness of the modified set of billing codes; and providing, by a coding output routing module executed by the at least one computer processor, a final coding output for a final review, wherein the final coding output comprises the medical chart, the modified code assessment data, and the modified set of billing codes, and wherein providing the final coding output for the final review results in correctness of errors in the modified set of billing codes received from the initial reviewer and increase in efficiency of a coding process, which lead to increase in accuracy of the final coding output and reduction in costs associated with the coding process; and (D) in response to determining that the medical chart describes a complex medical procedure:

providing the medical chart to the initial reviewer;

receiving the initial set of billing codes from the initial reviewer; and providing the initial set of billing codes for the final review, wherein providing the initial set of billing codes for the final review results in correctness of errors in the initial set of billing codes.

8. The system of claim 7, wherein the data representing the medical chart includes data representing a freeform text document.

9. The system of claim 7, wherein the data representing the medical chart includes data representing a structured document.

10. The system of claim 9, wherein the data representing the structured document comprises data representing an XML document.

11. The system of claim 7, wherein the data representing the medical chart comprises data representing a data record in a database.

12. The system of claim 7, wherein the data representing the medical chart includes data representing at least two of: a freeform text document, an XML document, and a data record in a database.

* * * * *